(12) United States Patent
Ishikawa et al.

(10) Patent No.: US 10,271,731 B2
(45) Date of Patent: Apr. 30, 2019

(54) OPTICAL BIOLOGICAL MEASUREMENT DEVICE AND ANALYSIS METHOD USING THE SAME

(75) Inventors: Akihiro Ishikawa, Kyoto (JP); Yoshihiro Inoue, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 53 days.

(21) Appl. No.: 14/416,412

(22) PCT Filed: Jul. 27, 2012

(86) PCT No.: PCT/JP2012/069209
§ 371 (c)(1),
(2), (4) Date: Jan. 22, 2015

(87) PCT Pub. No.: WO2014/016963
PCT Pub. Date: Jan. 30, 2014

(65) Prior Publication Data
US 2015/0201841 A1 Jul. 23, 2015

(51) Int. Cl.
*A61B 5/00* (2006.01)
*A61B 5/026* (2006.01)
*A61B 5/1455* (2006.01)

(52) U.S. Cl.
CPC .......... *A61B 5/0082* (2013.01); *A61B 5/0261* (2013.01); *A61B 5/14551* (2013.01); *A61B 5/14553* (2013.01); *A61B 5/4064* (2013.01); *A61B 5/6814* (2013.01); *A61B 5/7203* (2013.01)

(58) Field of Classification Search
CPC .................................. B41J 25/18; B41J 5/10
See application file for complete search history.

(56) References Cited

FOREIGN PATENT DOCUMENTS

| JP | 2005-245636 | 9/2005 |
|---|---|---|
| JP | 2012-32204 | 2/2012 |
| WO | WO 2012/005303 | 1/2012 |

OTHER PUBLICATIONS

PCT/JP2012/069209, International Search Report dated Aug. 21, 2012, 2 pages—Japanese, 1 page—English.

*Primary Examiner* — Hien N Nguyen
(74) *Attorney, Agent, or Firm* — Andrew F. Young, Esq.; Lackenbach Siegel, LLP

(57) ABSTRACT

An optical biological measuring device includes a light transmission/reception element 30 having a plurality of light transmission probes 12, light reception probes 13 and reference probes 14; a second observation signal acquiring element 25 for acquiring a second observation signal indicating a time-course variation relating to a cerebral activity; a first observation signal acquiring element 24 for acquiring a first observation signal indicating a time-course variation relating to the blood flow in the skin; and an analysis control element 40 for generating a removal target component removal observation signal based on the first and second observation signals.

9 Claims, 10 Drawing Sheets

Fig. 4

| Lighting time (msec) | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
|---|---|---|---|---|---|---|---|---|---|---|---|---|---|---|---|---|---|---|---|---|---|---|---|---|---|
| Light transmission probe to be lighted | T1 | T1 | T1 | T2 | T2 | T2 | T3 | T3 | T3 | T4 | T4 | T4 | T5 | T5 | T5 | T6 | T6 | T6 | T7 | T7 | T7 | T8 | T8 | T8 | – |
| Wavelength of probe (nm) | 780 | 805 | 830 | 780 | 805 | 830 | 780 | 805 | 830 | 780 | 805 | 830 | 780 | 805 | 830 | 780 | 805 | 830 | 780 | 805 | 830 | 780 | 805 | 830 | – |
| R1 |  | S1 |  |  | S2 |  |  | S5 |  |  | S7 |  |  |  |  |  |  |  |  |  |  |  |  |  | DARK |
| R2 |  |  |  |  |  | S3 |  |  |  |  |  |  |  |  |  |  |  |  |  |  |  |  |  |  | DARK |
| R3 |  | S4 |  |  |  |  |  | S8 |  |  |  |  |  | S11 |  |  | S13 |  |  |  |  |  |  |  | DARK |
| R4 |  |  |  |  | S6 |  |  |  |  |  | S10 |  |  | S15 |  |  | S16 |  |  |  |  |  |  |  | DARK |
| R5 |  |  |  |  |  |  |  | S9 |  |  |  |  |  |  |  |  |  |  |  | S19 |  |  | S21 |  | DARK |
| R6 |  |  |  |  |  |  |  | S12 |  |  | S14 |  |  | S18 |  |  | S17 |  |  |  |  |  |  |  | DARK |
| R7 |  |  |  |  |  |  |  |  |  |  |  |  |  |  |  |  | S20 |  |  | S22 |  |  |  |  | DARK |
| R8 |  |  |  |  |  |  |  |  |  |  |  |  |  |  |  |  |  |  |  | S23 |  |  | S24 |  | DARK |
| B1 |  | C1 |  |  |  |  |  |  |  |  |  |  |  |  |  |  |  |  |  |  |  |  |  |  | DARK |
| B2 |  |  |  |  |  |  |  | C2 |  |  |  |  |  |  |  |  |  |  |  |  |  |  |  |  | DARK |
| B3 |  |  |  |  | C3 |  |  |  |  |  |  |  |  |  |  |  |  |  |  |  |  |  |  |  | DARK |
| B4 |  |  |  |  |  |  |  |  |  |  | C4 |  |  | C5 |  |  |  |  |  |  |  |  |  |  | DARK |
| B5 |  |  |  |  |  |  |  | C6 |  |  |  |  |  |  |  |  |  |  |  |  |  |  |  |  | DARK |
| B6 |  |  |  |  |  |  |  |  |  |  |  |  |  |  |  |  | C7 |  |  |  |  |  |  |  | DARK |
| B7 |  |  |  |  |  |  |  |  |  |  | C8 |  |  |  |  |  |  |  |  |  |  |  |  |  | DARK |
| B8 |  |  |  |  |  |  |  |  |  |  |  |  |  | C9 |  |  |  |  |  |  |  |  |  |  | DARK |
| B9 |  |  |  |  |  |  |  |  |  |  |  |  |  |  |  |  |  |  |  | C10 |  |  |  |  | DARK |
| B10 |  |  |  |  |  |  |  |  |  |  |  |  |  |  |  |  | C11 |  |  |  |  |  |  |  | DARK |
| B11 |  |  |  |  |  |  |  |  |  |  |  |  |  |  |  |  |  |  |  |  |  |  | C12 |  | DARK |
| B12 |  |  |  |  |  |  |  |  |  |  |  |  |  |  |  |  |  |  |  |  |  |  |  |  | DARK |

Light reception probe in which data is acquired (a)

(b)

OPTICAL BIOLOGICAL MEASUREMENT DEVICE AND ANALYSIS METHOD USING THE SAME

CROSS REFERENCE TO RELATED APPLICATIONS

This application claims priority from and relates to International App. Ser. No. PCT/JP2012/069209 filed Jul. 27, 2012, the entire contents of which are incorporated herein by reference.

FIGURE SELECTED FOR PUBLICATION

FIG. 7

BACKGROUND OF THE INVENTION

Field of the Invention

The present invention relates to an optical biological measuring device using light and analysis method for acquiring an observation signal indicating time-course (chronological) variations in terms of a measurement site. Particularly, the present invention is used as an optical cerebral function imaging apparatus for measuring an activity situation of a cerebral measurement site in a noninvasive manner using near-infrared rays, and an oxygen monitor for monitoring oxygen consumption in a measurement site in a living body.

Description of the Related Art

In recent years, in order to observe a cerebral activity situation, optical cerebral function imaging apparatuses for conducting a measurement in a simple and noninvasive manner using light have been developed. In such optical cerebral function imaging apparatuses, the brain is irradiated with near infrared rays with three different wavelengths of $\lambda 1$, $\lambda 2$ and $\lambda 3$ (for example, 780 nm, 805 nm and 830 nm) from a light transmission probe arranged on the scalp surface of a subject, and intensity variations (information of an amount of received light) $\Delta A(\lambda_1)$, $\Delta A(\lambda_2)$ and $\Delta A(\lambda_3)$ of the near infrared rays with wavelengths of $\lambda 1$, $\lambda 2$ and $\lambda 3$ emitted from the brain are detected by light reception probes arranged on the scalp surface.

In order to obtain a product [oxyHb] of oxyhemoglobin concentration change and optical path length and a product [deoxyHb] of deoxyhemoglobin concentration change and optical path length in the cerebral blood flow from $\Delta A(\lambda 1)$, $\Delta A(\lambda 2)$, $\Delta A(\lambda 3)$, the information of the amount of received light obtained in this manner, for example, simultaneous equations shown by the relational equations (1), (2) and (3) are formulated by using, for example, Modified Beer Lambert Law, and then the simultaneous equations are solved. Further, a product ([oxyHb]+[deoxyHb]) of total hemoglobin concentration change and optical path length is calculated from the product [oxyHb] of oxyhemoglobin concentration change and optical path length and the product [deoxyHb] of deoxyhemoglobin concentration change and optical path length.

$$\Delta A(\lambda_1)=E_O(\lambda_1)\times[oxyHb]+E_d(\lambda_1)\times[deoxyHb] \quad (1)$$

$$\Delta A(\lambda_2)=E_O(\lambda_2)\times[oxyHb]+E_d(\lambda_2)\times[deoxyHb] \quad (2)$$

$$\Delta A(\lambda_3)=E_O(\lambda_3)\times[oxyHb]+E_d(\lambda_3)\times[deoxyHb] \quad (3)$$

$E_O(\lambda m)$ represents an absorbance coefficient of oxyhemoglobin at the light with wavelength $\lambda m$, and $E_d(\lambda m)$ represents an absorbance coefficient of deoxyhemoglobin at the light with wavelength $\lambda m$.

Here, a relationship between distance (channel) between the light transmission probe and the light reception probe and a measurement site is described. FIGS. 8A and 8B are diagrams illustrating a relationship between a pair of a light transmission probe and a light reception probe and a measurement site. A light transmission probe 12 is pressed against a light transmitting point T of the scalp surface of a subject, and a light reception probe 13 is pressed against a light receiving point R of the scalp surface of the subject. Light is irradiated from the light transmission probe 12, and then light emitted from the scalp surface is incident on the light reception probe 13. At this time, light that is radiated and passes through a banana-like shape region (measurement region) of the light radiated from the light transmitting point T of the scalp surface reaches the light receiving point R of the scalp surface.

Further, in the optical cerebral function imaging apparatuses, for example, a near-infrared spectrometer is used in order to measure the product [oxyHb] of oxyhemoglobin concentration change and optical path length, the product [deoxyHb] of deoxyhemoglobin concentration change and optical path length, and the product ([oxyHb]+[deoxyHb]) of total hemoglobin concentration change and optical path length related to a plurality of measurement sites in the brain.

In such a near-infrared spectrometer, a holder (transmission/reception portion) 130 is used in order to allow the eight light transmission probes 12 and the eight light reception probes 13 to contact with the scalp surface of a subject in a predetermined arrangement. FIG. 9 is a plan diagram illustrating one example of the holder 130 into which the eight light transmission probes and the eight light reception probes are inserted.

Light transmission probes $12_{T1}$ to $12_{T8}$ and light reception probes $13_{R1}$ to $13_{R8}$ are alternately arranged to make four in the vertical direction and the horizontal direction. At this time, a second setting distance r2 that is an interval (channel) between each of the light transmission probes $12_{T1}$ to $12_{T8}$ and each of the light reception probes $13_{R1}$ to $13_{R8}$ is 30 mm. As a result, the information of the amount of received light $\Delta A2_n(\lambda_1)$, $\Delta A2_n(\lambda_2)$ and $\Delta A2_n(\lambda_3)$ (n=1, 2, . . . , 24) concerning twenty-four measurement positions of the brain are obtained.

The twenty-four information of the amount of received light $\Delta A2_n(\lambda_1)$, $\Delta A2_n(\lambda_2)$ and $\Delta A2_n(\lambda_3)$ are obtained at a predetermined time interval $\Delta t$ so that time-course (chronological) variations (second observation signal) $X_n(t)$ of the product [oxyHb] of oxyhemoglobin concentration change and optical path length, time-course variations (second observation signal) $Y_n(t)$ of the [deoxyHb] of deoxyhemoglobin concentration change and optical path length, and time-course variations (second observation signal) $Z_n(t)$ of the product ([oxyHb]+[deoxyHb]) of total hemoglobin concentration change and optical path length (n=1, 2, . . . , 24) are obtained by using the relational equations (1), (2) and (3).

FIG. 5 is a diagram illustrating a monitor screen where twenty-four time-course variations (second observation signals) $X_n(t)$ of the product [oxyHb] of oxyhemoglobin concentration change and optical path length are being displayed. Further, the vertical axis in one of second observation signal $X_n(t)$ represents the product [oxyHb] of oxyhemoglobin concentration change and optical path length, and the horizontal axis represents time t.

Incidentally, as shown in FIG. 5, the displayed twenty-four of second observation signals $X_n(t)$ include overlapping signals based on the fluctuations in the blood flow in the skin, the heart rate, variations in pulsation and respiration and so forth, in addition to signals based on the blood flow according to the brain activity.

Therefore, in order to easily diagnose whether or not symptoms such as cerebral ischemia are generated, a biological light measuring method for surely discriminating the signals based on the blood flow according to the brain activity from signals other than these signals in the second observation signal $X_n(t)$ is disclosed (for example, see Patent Document 1). Such a biological light measuring method includes a step (a) of obtaining an N×N mixing matrix and numerical N independent component signals $S_n(t)$ based on observation signals $X_n(t)$ on numerical N detection positions through independent component analysis (ICA) according to the following formula (4); a step (b) of substituting 0 for a column vector corresponding to a removal target component in the N×N mixing matrix as expressed in the following formula (5); and a step (c) of calculating a product of the N×N removal target component removal mixing matrix and numerical N independent component signals $S_n(t)$ so as to obtain numerical N removal target component removal observation signals $X_n'(t)$.

[Mathematical Formula 1]

$$\underset{\text{signal}}{\underset{\text{observation}}{\begin{pmatrix} X_1(t) \\ X_2(t) \\ \vdots \\ X_n(t) \end{pmatrix}}} = \underset{\text{mixing matrix}}{\begin{pmatrix} a_{11} & a_{12} & \cdots & a_{1n} \\ a_{21} & a_{12} & \cdots & a_{2n} \\ \vdots & \vdots & \ddots & \vdots \\ a_{n1} & a_{n2} & \cdots & a_{nn} \end{pmatrix}} \underset{\text{component signal}}{\underset{\text{independent}}{\begin{pmatrix} S_1(t) \\ S_2(t) \\ \vdots \\ S_n(t) \end{pmatrix}}} \quad (4)$$

The column vector in the mixing matrix represents a weight of a specific independent component signal $S_n(t)$ in a measurement site. That is to say, the observation signals $X_n(t)$ are a linear combination of numerical N independent component signals $S_n(t)$ from independent signal generating sources with respective elements in the mixing matrix as a weight coefficient.

[Mathematical Formula 2]

$$\underset{\substack{\text{Removal target} \\ \text{component} \\ \text{removal} \\ \text{observation signal}}}{\begin{pmatrix} X_1'(t) \\ X_2'(t) \\ \vdots \\ X_n'(t) \end{pmatrix}} = \underset{\substack{\text{Removal} \\ \text{target component} \\ \text{removal} \\ \text{mixing matrix}}}{\begin{pmatrix} 0 & a_{12} & \cdots & a_{1n} \\ 0 & a_{12} & \cdots & a_{2n} \\ 0 & \vdots & \ddots & \vdots \\ 0 & a_{n2} & \cdots & a_{nn} \end{pmatrix}} \underset{\substack{\text{Independent} \\ \text{component signal}}}{\begin{pmatrix} S_1(t) \\ S_2(t) \\ \vdots \\ S_s(t) \end{pmatrix}} \quad (5)$$

The expression (5) shows a case where an independent component signal $S_1(t)$ is determined as a removal target component, 0 is substituted for a first column vector corresponding to the removal target component, and a removal target component removal mixing matrix is generated.

According to such a biological light measuring method, the removal target component removal observation signals $X_n'(t)$ can be restored, in which the signal $S_1(t)$ based on the removal target component from the observation signals $X_n(t)$ is removed.

On the other hand, in order to acquire the information of the amount of received light ΔA only based on a blood vessel in the brain, that having a distance (channel) between the light transmission probe 12 and the light reception probe 13 is set as both a short distance r1 and a long distance r2 is disclosed (for example, see Patent Document 2 and Non-Patent Document 1.) FIG. 10 is a cross-sectional diagram illustrating a relationship between the light transmission probe 12 to make a short distance r1 with a reference probe 14 and a long distance r2 with the light reception probe 13 and a measurement site. As a result, second information of the amount of received light ΔA2 about a blood vessel present in the skin near the light transmitting point T, a blood vessel present in the brain and a blood vessel present in the skin in proximity to the light receiving point R2 is acquired at the long distance r2 channel, and first information of the amount of received light ΔA1 about only a blood vessel present in the skin in proximity to the light transmitting point T (blood vessel present in the skin in proximity to a light receiving point R1) is acquired at the short distance r1 channel.

The information of the amount of received light ΔA about only the blood vessel present in the brain is obtained based on the information of the amount of received light ΔA1 and ΔA2 by using the equation (6).

$$\Delta A = \Delta A2 - K\Delta A1 \quad (6)$$

Incidentally, in the equation (6), a coefficient K should be determined in order to obtain the information of the amount of received light ΔA, and a method for calculating the coefficient K is disclosed (for example, see Non-Patent Document 2.) In this calculating method, the coefficient K is calculated by using least square error.

PRIOR ART DOCUMENT

Patent Documents

Patent Document 1: JP 2005-245636 A
Patent Document 2: JP 2009-136434 A

Non-Patent Documents

Non-Patent Document 1: Rolf B. Saager, and Andrew J. Berger "Direct characterization and removal of interfering absorption trends in two-layer turbid media" J. Opt. Soc. Am. A/Vol. 22, No. 9/September 2005.

Non-Patent Document 2: Francesco Fabbri, Angelo Sassaroli, Michael e Henry, and Sergio Fantini "Optical measurements of absorption changes in two-layered diffusive media" Phys. Med. Biol. 49(2004) 1183-1201.

ASPECTS AND SUMMARY OF THE INVENTION

Aspects to be Solved

The optical biological measuring device using above independent component analysis, however, utilizes signals based on the blood flow in the skin, which are not localized, it is effective only on the wide range measurement of the brain but no precise diagnosis whether a cerebral ischemia have taken place or not might be achieved when the local cerebral area was measured.

Further in the above calculation method using information of an amount of received light ΔA1, ΔA2 and the coefficient K, the calculated information of the amount of received light ΔA was obtained under consideration of the combination of a pair of a light transmission probe 12 and a light reception probe 13 but not under consideration of the combination of a plurality of light transmission probes $12_{T1}$ to $12_{T8}$ and a plurality of light reception probes $13_{R1}$ to $13_{R8}$ as the holder 130 of the above optical cerebral function imaging apparatus. Further, the first information of the amount of received light ΔA1 includes most of signals based on the blood flow in the skin but also includes signals based on the blood flow along with brain activities despite an extremely small amount. Accordingly, an object of the present invention is to provide an optical biological measuring device and a method of analysis using the same, in which a signal corresponding to a removal target component can be removed from the observed signals even when a local area of brain is measured.

Means to Solve the Concerns

In one aspect of the invention, disclosed is an optical biological measuring device including a light transmission/reception element 30 having a plurality of light transmission probes 12, light reception probes 13 and reference probes 14; a second observation signal acquiring element 25 for acquiring a second observation signal indicating a time-course variation relating to a cerebral activity; a first observation signal acquiring element 24 for acquiring a first observation signal indicating a time-course variation relating to the blood flow in the skin; and an analysis control element 40 for generating a removal target component removal observation signal based on the first and second observation signals, the analysis control element 40 includes a second mixing matrix generating element 44 for separating a plurality of second observation signal into products of a second mixing matrix and a plurality of second independent component signals through independent component analysis, a removal target second independent component signal determination element 46 for extracting a removal target second independent component signal from among the plurality of second independent component signals using the first observation signal, and a restructuring element 47 for removing a removal target second observation signal so as to generate a plurality of removal target component removal observation signals.

In order to solve the above problem, the optical biological measuring device of the present invention includes a light transmission/reception element having a plurality of light transmission probes arranged on the scalp surface of a subject, a plurality of light reception probes arranged on positions separated from the light transmission probes on the scalp surface by a second setting distance r2, and reference probes arranged on positions separated from the light transmission probes or the light reception probes on the scalp surface by a first setting distance r1 shorter than the second setting distance r2; a second observation signal acquiring element for acquiring second information of an amount of received light ΔA2 from the light transmission probes to the light reception probes so as to acquire a second observation signal indicating a time-course (chronological) variation relating to a cerebral activity; a first observation signal acquiring section for acquiring first information of an amount of received light ΔA1 from the light transmission probes or the light reception probes to the reference probes so as to acquire a first observation signal indicating a time-course variation relating to the blood flow in the skin; and an analysis control element for generating a removal target component removal observation signal based on the first observation signal and the second observation signal, wherein the analysis control element includes a second mixing matrix generating element for separating a plurality of second observation signals into products of a second mixing matrix and a plurality of second independent component signals through independent component analysis, a removal target second independent component signal determination element for finding a removal target second independent component signal from among the plurality of second independent component signals using the first observation signal, and a restructuring element for removing the removal target second independent component signal from the second observation signal so as to generate a plurality of removal target component removal observation signals.

Herein, "the second setting distance r2" is a distance for acquiring information of an amount of received light about a blood vessel present in the skin in proximity to the light transmitting point T, a blood vessel present in the brain and a blood vessel present in the skin in proximity to the light receiving point R, and "the first setting distance r1" is a distance for acquiring information of an amount of received light about the blood vessel present in the skin in proximity to the light sending point T or the light receiving point R.

Further, "the observation signal" may be a time-course variation itself in the information of the amount of received light detected by the light reception probes, or may be a time-course variation in oxyhemoglobin concentration calculated based on the information of the amount of received light, or a time-course variation in deoxyhemoglobin concentration or a time-course variation in total hemoglobin concentration.

Furthermore, "the signal corresponding to the removal target component" refers to a signal other than the signal based on the blood flow according to the brain activity, and for example, refers to the signal based on the blood flow in the skin, the signal based on the fluctuations in the heart rate, and the signal based on pulsation and respiration and so forth.

In the optical biological measuring device of the present invention, the second observation signal acquiring element allows the light transmission probe to irradiate the scalp surface with light and control the light reception probe in order to detect light emitted from the scalp surface, and thus numerical N second observation signals $X_n(t)$ concerning numerical N measurement sites are acquired. Here, the second observation signals $X_n(t)$ include overlapping signals based on the fluctuations in the blood flow in the skin and the heart rate and variations in pulsation and respiration and so forth, in addition to signals based on the blood flow according to the brain activity.

Therefore, the analysis control element removes the signal corresponding to the removal target component from the second observation signals $X_n(t)$. First, the second mixing matrix generating element, as shown by the formula (4), separates numerical N second observation signals $X_n(t)$ into products of an N×N second mixing matrix and numerical N second independent component signals $S_n(t)$ through independent component analysis. Herein, when there is a signal generating source of the signal based on the blood flow in the skin, which is irrelevant of the signal based on the blood flow according to the brain activity, it is considered that any of numerical N second independent component signals $S_n(t)$ is the signal based on the blood flow in the skin from the signal generating source. The number of signals to be determined as the signals corresponding to the removal target component is not limited to one, and may be two or more.

Next, in order to find the signal based on the blood flow in the skin from among numerical N second independent component signals $S_n(t)$, the first observation signal acquiring element allows the light transmission probe to irradiate the scalp surface with light and control the reference probe in order to detect light emitted from the scalp surface, and thus at least one first observation signal H(t) concerning at least one measurement site is acquired. The first observation signal H(t) mostly includes the signal based on the blood flow in the skin.

The removal target second independent component signal determination element compares at least one first observation signal H(t) with numerical N second independent component signals $S_n(t)$, so as to find the removal target second independent component signal from among numerical N second independent component signals $S_n(t)$. For example, the second independent component signal $S_1(t)$ is found as the removal target second independent component signal.

Finally, as shown by the formula (5), the restructuring element generates an N×N removal target component removal mixing matrix where 0 is substituted for a column vector corresponding to a removal target second independent component signal $S_1(t)$ in the N×N mixing matrix, and calculates the products of the N×N removal target component removal mixing matrix and numerical N second independent component signals $S_n(t)$ so as to obtain numerical N removal target component removal observation signals $X_n'(t)$.

Effects of the Invention

As described above, in the optical biological measuring device of the present invention, since the removal target second independent component signal $S_1(t)$ is found from among numerical N second independent component signals $S_n(t)$ by using the first observation signals H(t) almost all of which includes the signal based on the blood flow in the skin, it is possible to accurately diagnose whether or not symptoms such as cerebral ischemia are generated also in the case of regionally measuring the brain.

Further, in the optical biological measuring device of the present invention, a plurality of reference probes is arranged in the light transmission/reception element, and the analysis control element includes a first mixing matrix generating element for separating a plurality of first observation signals into products of a first mixing matrix and a plurality of first independent component signals through independent component analysis, and a removal target first independent component signal determination element for finding a removal target first independent component signal from among the plurality of first independent component signals. The removal target second independent component signal determination element calculates correlation coefficients between the removal target first independent component signals and the second independent component signals, and may determine a signal where the correlation coefficient is a threshold or more as the removal target second independent component signal.

In the optical biological measuring device of the present invention, the first observation signal acquiring element allows the light transmission probe to irradiate the scalp surface with light and control the reference probe in order to detect light emitted from the scalp surface, and thus numerical M first observation signals $H_m(t)$ concerning numerical M measurement sites are acquired. The first observation signals $H_m(t)$ mostly include the signal based on the blood flow in the skin, but few of them include the signal based on the blood flow according to the brain activity.

Therefore, the analysis control element finds the signal corresponding to the removal target component from among the first observation signals $H_m(t)$. Also at this time, the independent component analysis is used. First, the first mixing matrix generating element, as shown by the following formula (7), separates numerical M first observation signals $H_m(t)$ into products of an M×M first mixing matrix and numerical M first independent component signals $U_m(t)$ through independent component analysis. Herein, when there is a signal generating source of the signal based on the blood flow in the skin, which is irrelevant of the signal based on the blood flow according to the brain activity, it is considered that any of numerical M second independent component signals $U_m(t)$ is the signal based on the blood flow in the skin from the signal generating source. The number of signals to be determined as the signals corresponding to the removal target component is not limited to one, and may be two or more.

[Mathematical Formula 3]

$$\underset{\text{First observation signal}}{\begin{pmatrix} H1(T) \\ H2(T) \\ \vdots \\ Hm(T) \end{pmatrix}} = \underset{\text{First mixing matrix}}{\begin{pmatrix} b11 & b12 & \ldots & b1m \\ b21 & b22 & \ldots & b2m \\ \vdots & & \ddots & \vdots \\ bm1 & bm2 & & bmm \end{pmatrix}} \underset{\text{First independent component signal}}{\begin{pmatrix} U1(T) \\ U2(T) \\ \vdots \\ Um(T) \end{pmatrix}} \quad (7)$$

Next, the removal target first independent component signal determination element finds a removal target first independent component signal from among numerical M first independent component signals $U_m(t)$. For example, as shown by the following formula (8), the maximum mixing coefficient $b_{max}$ is found from among each line vector in the M×M first mixing matrix so as to be circled, and the removal target first independent component signal is found based on the number of the maximum mixing coefficients $b_{max}$ present in each column vector (for example, 2 or more), and threshold mixing coefficients $b_{over}$ that are a threshold $b_{th}$ or more is found from among each line vector in the M×M first mixing matrix. The removal target first independent component signal is found based on the number of the threshold mixing coefficients $b_{over}$ present in each column vector (for example, 2 or more).

[Mathematical Formula 4]

$$\underset{\text{First observation signal}}{\begin{pmatrix} H1(T) \\ H2(T) \\ \vdots \\ Hm(T) \end{pmatrix}} = \underset{\text{First mixing matrix}}{\begin{pmatrix} b11 & \boxed{b12} & \cdot & b1m \\ \boxed{b21} & b22 & \cdot & b2m \\ \cdot & \boxed{\cdot} & \cdot & \cdot \\ bm1 & \boxed{bm2} & \cdot & bmm \end{pmatrix}} \underset{\text{First independent component signal}}{\begin{pmatrix} U1(T) \\ U2(T) \\ \vdots \\ Um(T) \end{pmatrix}} \quad (8)$$

$$\downarrow \quad \downarrow \quad \downarrow \quad \downarrow$$
$$\phantom{xxx} 1 \quad 8 \quad \cdot \quad 0$$

The formula (8) shows a case where the number of the maximum mixing coefficients $b_{max}$ present in the second column vector is two or more and a first independent component signal $U_2(t)$ is the removal target first independent component signal.

The removal target second independent component signal determination element calculates correlation coefficients $\alpha_n$ between a removal target first independent component signal $U_2(t)$ and numerical N second independent component signals $S_n(t)$, and determines signals where correlation coefficients $\alpha_n$ are a threshold $\alpha_{th}$ or more as the removal target second independent component signal. For example, when the correlation coefficients $\alpha_n$ between the second independent component signal $S_1(t)$ and the removal target first independent component signal $U_2(t)$ is the threshold $\alpha_{th}$ or more, the second independent component signal $S_1(t)$ is found as the removal target second independent component signal.

As described above, in the optical biological measuring device of the present invention, the independent component analysis is conducted on numerical M first observation signals $H_m(t)$ so that the removal target first independent component signal $U_2(t)$ is found from among numerical M first independent component signals $U_m(t)$, and further, the removal target second independent component signal $S_1(t)$ is found from among numerical N second independent component signals $S_n(t)$ by using the removal target first independent component signal $U_2(t)$. For this reason, it is possible to accurately diagnose whether or not symptoms such as cerebral ischemia are generated also in the case of regionally measuring the brain.

Further, in the optical biological measuring device of the present invention, the removal target first independent component signal determination element may find the maximum mixing coefficient from among each line vector in the first mixing matrix, and may find the removal target first independent component signal based on the number of the maximum mixing coefficients present in each column vector.

Further, in the optical biological measuring device of the present invention, the removal target first independent component signal determination element may find the threshold mixing coefficient that is the threshold or more from among each line vector in the first mixing matrix, and may find the removal target first independent component signal based on the number of the threshold mixing coefficients present in each column vector.

Further, in the optical biological measuring device of the present invention, the restructuring element substitutes 0 for a column vector corresponding to the removal target second independent component signal in the second mixing matrix so as to generate the removal target component removal mixing matrix, and multiplies the removal target component removal mixing matrix by the plurality of second independent component signals, so as to generate a plurality of removal target component removal observation signals.

The analysis method of the present invention for generating a removal target component removal observation signal based on a first observation signal and a second observation signal using an optical biological measuring device including a light transmission/reception element having a plurality of light transmission probes arranged on the scalp surface of a subject, a plurality of light reception probes arranged on positions separated from the light transmission probes on the scalp surface by a second setting distance r2, and reference probes arranged on positions separated from the light transmission probes or the light reception probes on the scalp surface by a first setting distance r1 shorter than the second setting distance r2; a second observation signal acquiring element for acquiring second information of an amount of received light $\Delta A2$ from the light transmission probes to the light reception probes so as to acquire the second observation signal indicating a time-course variation relating to a cerebral activity; and a first observation signal acquiring element for acquiring first information of an amount of received light $\Delta A1$ from the light transmission probes or the light reception probes to the reference probes so as to acquire the first observation signal indicating a time-course variation relating to the blood flow in the skin, wherein the analysis method includes a second mixing matrix generating step of separating a plurality of second observation signals into products of a second mixing matrix and a plurality of second independent component signals through independent component analysis; a removal target second independent component signal determining step of finding a removal target second independent component signal from among the plurality of second independent component signals using the first observation signal; and a restructuring step of removing the removal target second independent component signal from the second observation signal so as to generate a plurality of removal target component removal observation signals.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 4 is a diagram for describing one example of a control table.

DETAILED DESCRIPTION OF THE PREFERRED EMBODIMENTS

Figure 1:
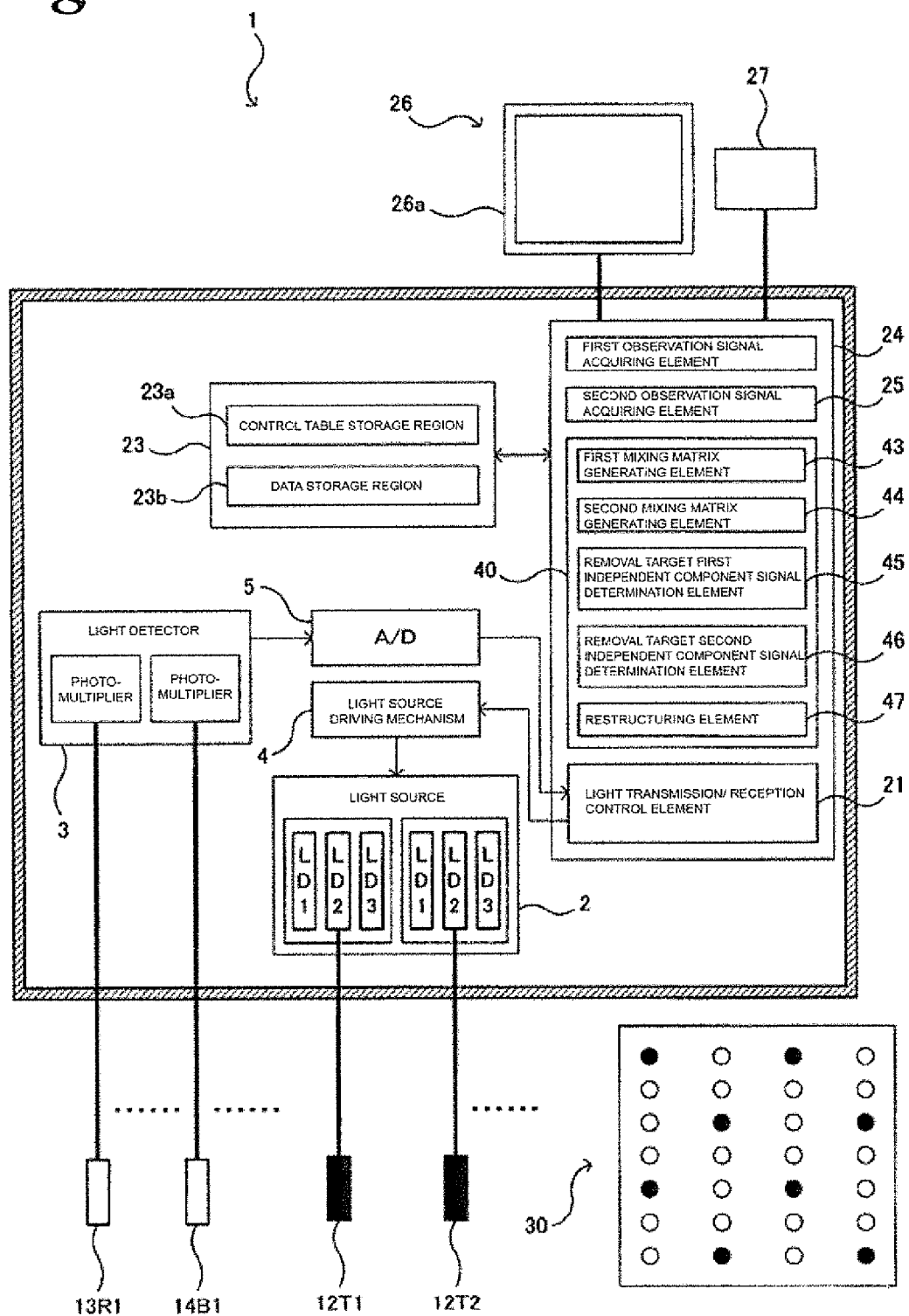
FIG. 1 is a block diagram illustrating a schematic structure of an optical biological measuring device according to one embodiment of the present invention.

Reference will now be made in detail to embodiments of the invention. Wherever possible, same or similar reference numerals are used in the drawings and the description to refer to the same or like parts or steps. The drawings are in simplified form and are not to precise scale. The words 'couple' connected 'linked' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. It will be further understood that certain terms, such as 'data' may be plural or singular a suited to the circumstance, and that there shall be no limitation on such use, so that 'a data' or 'the data' or simply 'data' may be plural or singular. It will also be understood that the phrases 'time-course' or 'chronological' will be understood as relative terms of the process and steps discussed herein and are not to be construed in a limiting manner. All these and the related terms used in the application should not be construed to limit or narrow the scope in any manner. It will also be understood that other embodiments may be utilized without departing from the scope of the present invention, and that the detailed description is not to be taken in a limiting sense, and that elements may be differently positioned, or remotely located (and operable via distant electronic connection) or otherwise noted as in the appended claims without need of the written description being required thereto.

In the following, the embodiments of the present invention are described in reference to the drawings. Here, the present invention is not limited to the following embodiments, but includes various aspects within the range that does not deviate from the gist of the present invention.

Figure 2:
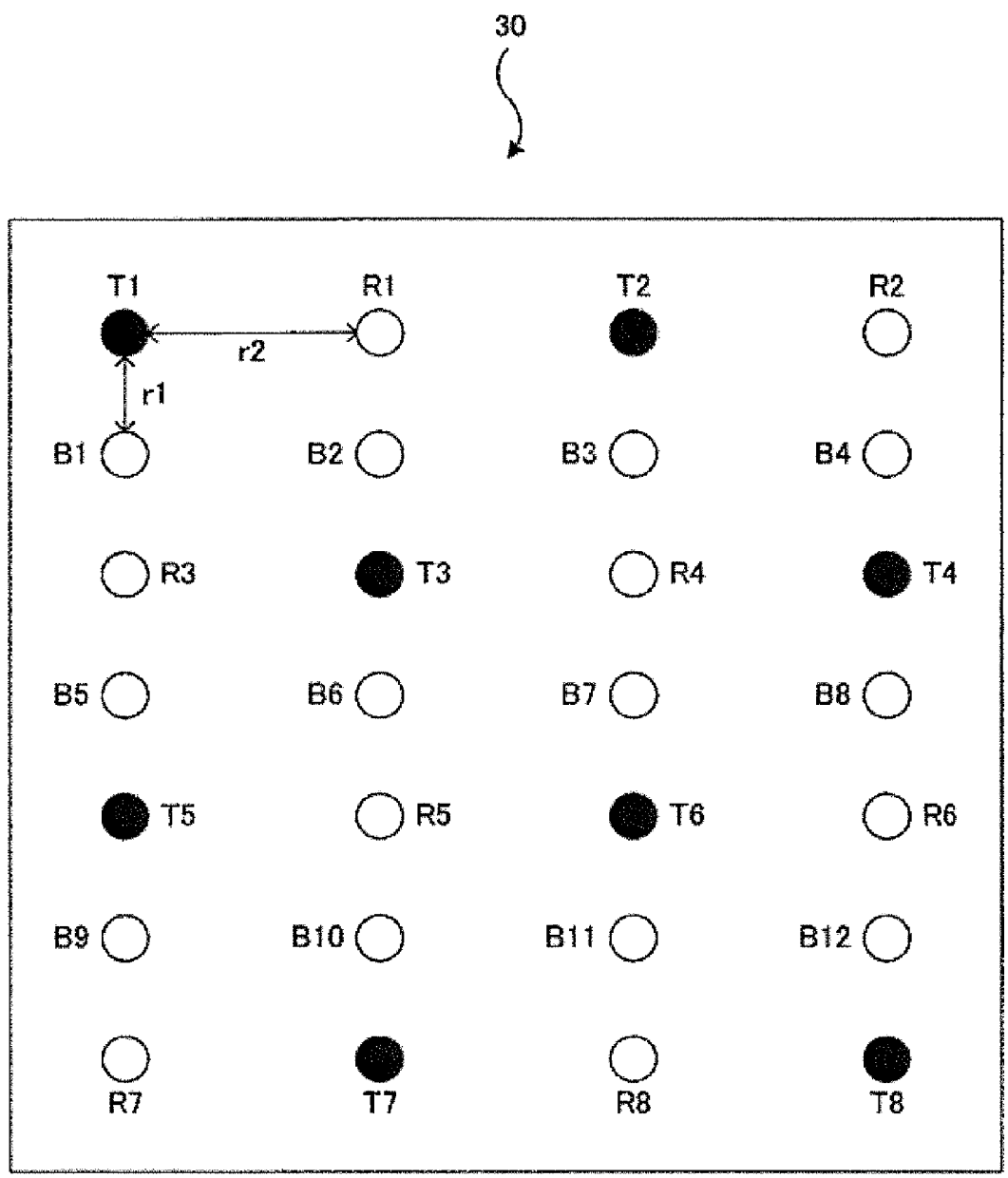
FIG. 2 is a plan diagram illustrating one example of a holder into which eight light transmission probes, eight light reception probes and twelve reference probes are inserted.

FIG. 1 is a block diagram illustrating a schematic structure of an optical biological measuring device according to one embodiment of the present invention. Further, FIG. 2 is a plan diagram illustrating one example of a holder (light transmission/reception element) into which eight light transmission probes, eight light reception probes and twelve reference probes are inserted.

An optical biological measurement device 1 includes a light source 2 for emitting light, a light source driving mechanism 4 for driving the light source 2, a light detector 3 for detecting light, an A/D (A/D converter) 5, a light transmission/reception control element 21, a first observation signal acquiring element 24 for calculating first observation signals $U_m(t)$, a second observation signal acquiring element 25 for calculating second observation signals $X_n(t)$, an analysis control element 40, and a memory 23, as well as eight light transmission probes 12, eight light reception probes 13, twelve reference probes 14, a holder 30, a display device 26 having a monitor screen 26a, etc., and a keyboard 27.

The light source driving mechanism 4 drives the light source 2 based on a driving signal input from the light transmission/reception control element 21. The light source 2 is, for example, semiconductor lasers LD1, LD2 and LD3 that can emit three different kinds of near infrared rays with wavelengths of $\lambda_1$, $\lambda_2$ and $\lambda_3$.

The light detector 3 is, for example, a photo multiplier, and detects near infrared rays received by the eight light reception probes $13_{R1}$ to $13_{R8}$ individually, so as to output eight second information of an amount of received light $\Delta A2(\lambda_1)$, $\Delta A2(\lambda_2)$ and $\Delta A2(\lambda_3)$ to the light transmission/reception control element 21 via the A/D 5. The light detector 3 also detects near infrared rays received by the twelve reference probes 14 individually, so as to output twelve first information of an amount of received light $\Delta A1(\lambda_1)$, $\Delta A1(\lambda_2)$ and $\Delta A1(\lambda_3)$ to the light transmission/reception control element 21 via the A/D 5.

The holder 30 has the eight light transmission probes $12_{T1}$ to $12_{T8}$, the eight light reception probes $13_{R1}$ to $13_{R8}$, and the twelve reference probes $14_{B1}$ to $14_{B12}$.

The light transmission probes $12_{T1}$ to $12_{T8}$ and the light reception probes $13_{R1}$ to $13_{R8}$ are arranged into a square lattice pattern alternately in a line direction and a column direction. At this time, a second setting distance r2 that is an interval (channel) between each of the light transmission probes $12_{T1}$ to $12_{T8}$ and each of the light reception probes $13_{R1}$ to $13_{R8}$ is 30 mm.

Further, the reference probe $14_{B1}$ is arranged on a position between the light transmission probe $12_{T1}$ and the light reception probe $13_{R3}$, the reference probe $14_{B1}$ being separated from the light transmission probe $12_{T1}$ by a first setting distance r1. A first setting distance r1 that is an interval between the light transmission probe $12_{T1}$ and the reference probes $14_{B1}$ is 15 mm. The respective reference probes 14 are arranged on positions separated from the respective light transmission probes 12 by the first setting distance r1 such that the reference probe $14_{B2}$ is arranged on a position separated from the light transmission probe $12_{T3}$ by the first setting distance r1, and the reference probes $14_{B3}$ is arranged on a position separated from the light transmission probe $12_{T2}$ by the first setting distance r1.

The memory 23 is formed with a control table storage region 23a to store a control table in which control forms for controlling transmission/reception of light are set in advance for the holder 30 in order to acquire twenty-four second information of an amount of received light $\Delta A2_n(\lambda_1)$, $\Delta A2_n(\lambda_2)$ and $\Delta A2_n$ and twelve first information of an amount of received light $\Delta A1_m(\lambda_1)$, $\Delta A1_m(\lambda_2)$ and $\Delta A1_m(\lambda_3)$; and a data storage region 23b for storing the twenty-four second information of the amount of received light $\Delta A2_n(\lambda_1)$, $\Delta A2_n(\lambda_2)$ and $\Delta A2_n$, the twelve first information of the amount of received light $\Delta A1_m(\lambda_1)$, $\Delta A1_m(\lambda_2)$ and $\Delta A1_m(\lambda_3)$, etc.

Figure 3:
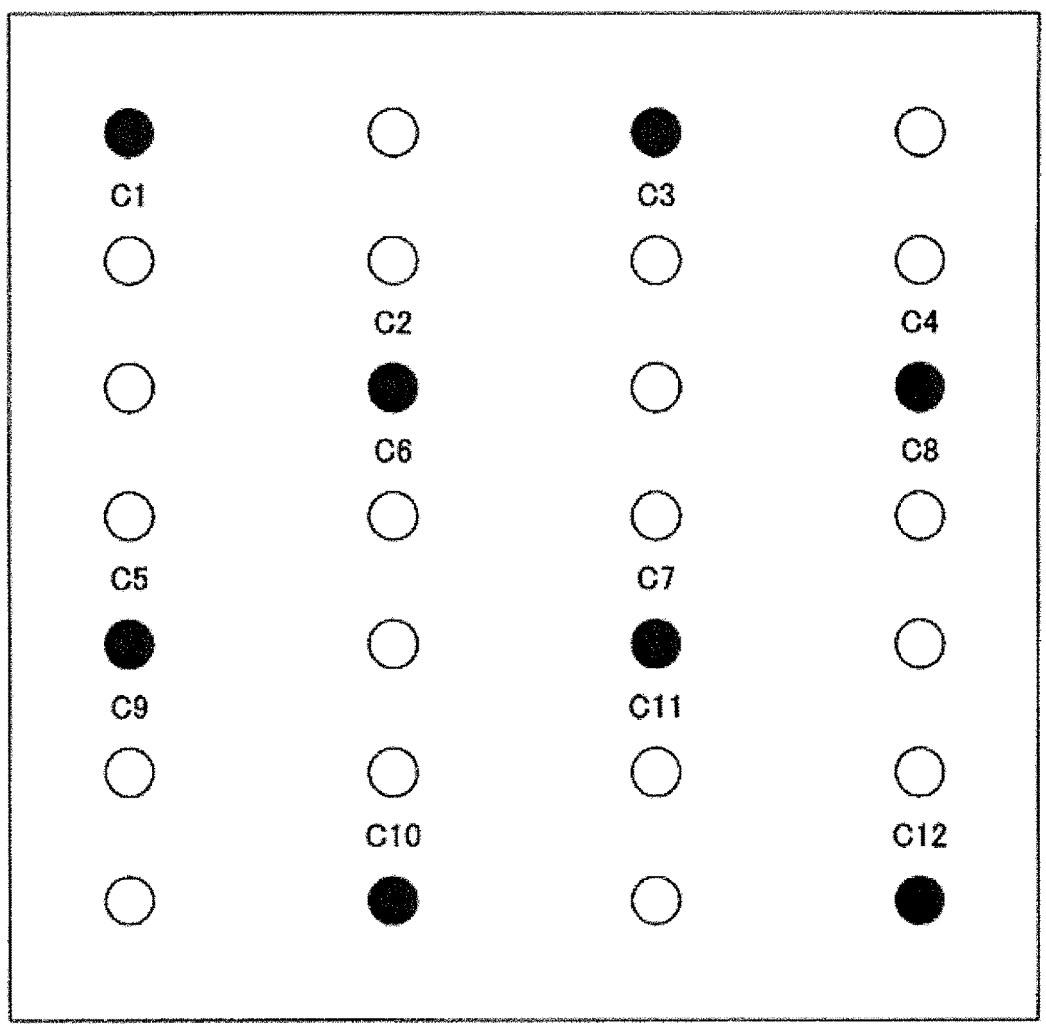
FIG. 3 is a diagram for describing positions where first information of an amount of received light is obtained.
Figure 5:
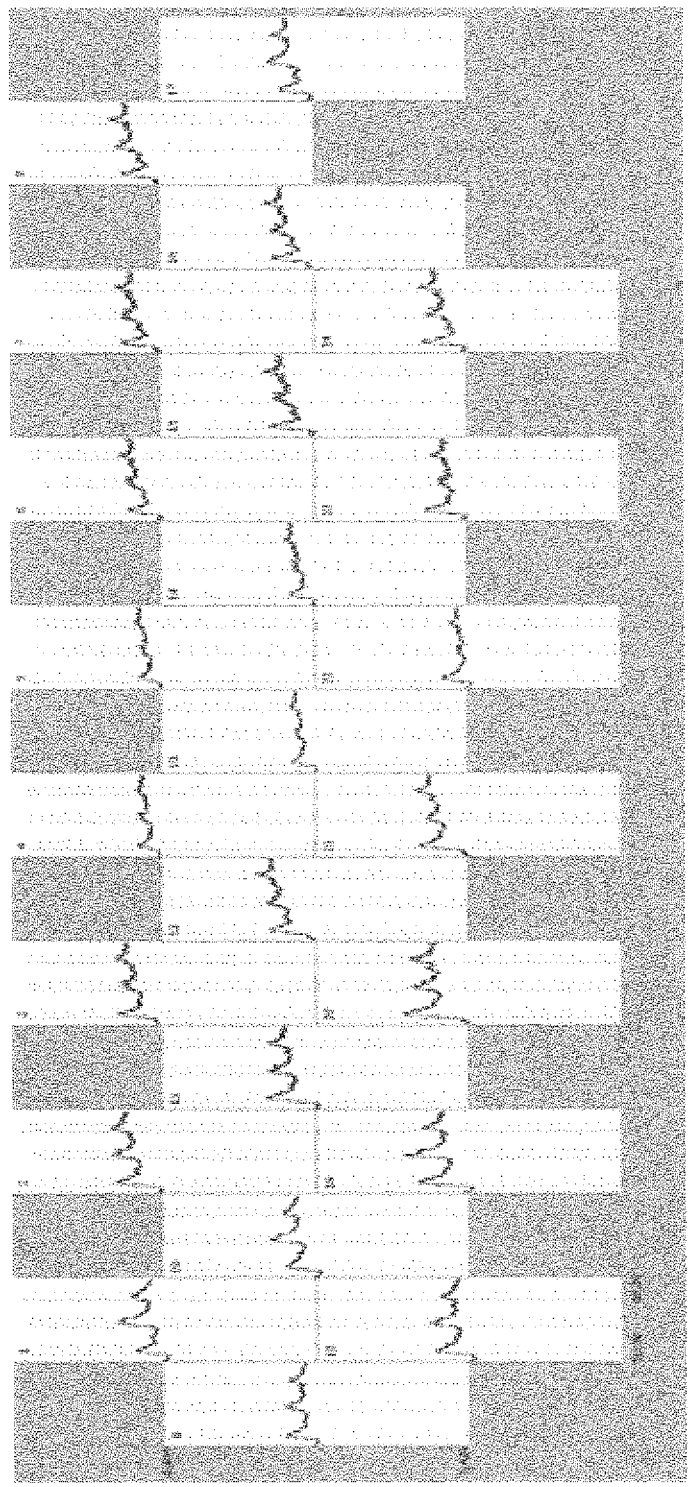
FIG. 5 is a diagram illustrating a monitor screen on which time-course (chronological) variations (second observation signals) $X_n(t)$ of a product [oxyHb] of concentration change of twenty-four oxyhemoglobins and optical path length are displayed.

Here, FIG. 3 is a diagram for describing a position where the first information of the amount of received light is obtained, and FIG. 4 is a diagram for describing one example of the control table. According to such a control table, light is sequentially transmitted to each of the light transmission probes $12_{T1}$ to $12_{T8}$ at predetermined timing such that light with a wavelength of 780 nm is transmitted to the light transmission probe $12_{T1}$ for first 5 milliseconds, light with a wavelength of 805 nm is transmitted to the light transmission probe $12_{T1}$ for next 5 milliseconds, light with a wavelength of 830 nm is transmitted to the light transmission probe $12_{T1}$ for next 5 milliseconds, and light with a wavelength of 780 nm is transmitted to the light transmission probe $12_{T2}$ for next 5 milliseconds. At this time, every time when light is transmitted to any one of the light transmission probes $12_{T1}$ to $12_{T8}$, the eight light reception probes $13_{R1}$ to $13_{R8}$ and the twelve reference probes $14_{B1}$ to $14_{B12}$ detect information of an amount of received light, but predetermined information of an amount of received light about the light reception probes $13_{R1}$ to $13_{R8}$ and predetermined information of an amount of received light about the reference probes $14_{B1}$ to $14_{B12}$ that are detected at predetermined timing are stored in the data storage region 23b of the memory 23. Concretely, the predetermined information of the amount of received light about the light reception probes $13_{R1}$ to $13_{R8}$ and the predetermined information of the amount of received light about the reference probes $14_{B1}$ to $14_{B12}$ that are detected at predetermined timing are stored in the data storage region 23b such that information of an amount of received light about the light reception probe $13_{R1}$, the light reception probe $13_{R3}$, and the reference probe $14_{B1}$ that detect light from the light transmission probe $12_{T1}$ is stored in the data storage region 23b, and information of an amount of received light about the light reception probe $13_{R1}$, the light reception probe $13_{R2}$, the light reception probe $13_{R4}$, and the reference probe $14_{B3}$ that detect light from the light transmission probe $12_{T2}$ is stored in the data storage region 23b. As a result, the twenty-four second information of the amount of received light $\Delta A2_n(\lambda_1)$, $\Delta A2_n(\lambda_2)$, and $\Delta A2_n(\lambda_3)$ in total are collected, and the twelve first information of the amount of received light $\Delta A1_m(\lambda_1)$, $\Delta A1_m(\lambda_2)$, and $\Delta A1_m(\lambda_3)$ in total are collected.

The light transmission/reception control element 21 controls output of a driving signal for transmitting light to one light transmission probe 12 to the light source driving mechanism 4 at a predetermined time based on the control table, and detection of the information of the amount of received light $\Delta A1_m(\lambda_1)$, $\Delta A1_m(\lambda_2)$, $\Delta A1_m(\lambda_3)$, $\Delta A2_n(\lambda_1)$, $\Delta A2_n(\lambda_2)$, and $\Delta A2_n(\lambda_3)$ (m=1, 2, ..., 12, and n=1, 2, ..., 24), with the photodetector 3, received by the light reception probes 13 and the reference probes 14.

The first observation signal acquiring element 24 controls obtainment of time-course variations (first observation signal) $H_m(t)$ of a product [oxyHb] of oxyhemoglobin concentration change and optical path length, time-course variations (first observation signal) $I_m(t)$ of a product [deoxyHb] of deoxyhemoglobin concentration change and optical path length, and time-course variations (first observation signal) $J_m(t)$ of a product ([oxyHb]+[deoxyHb]) of total hemoglobin concentration change and optical path length (m=1, 2, ..., 12) based on the twelve first information of the amount of received light $\Delta A1_m(\lambda_1)$, $\Delta A1_m(\lambda_2)$ and $\Delta A1_m(\lambda_3)$ stored in the data storage region 23b by using the relational equations (1), (2) and (3).

The second observation signal acquiring element 25 controls obtainment of time-course variations (second observation signal) $X_n(t)$ of a product [oxyHb] of oxyhemoglobin concentration change and optical path length, time-course variations (second observation signal) $Y_n(t)$ of a product [deoxyHb] of deoxyhemoglobin concentration change and optical path length, and time-course variations (second observation signal) $Z_n(t)$ of a product ([oxyHb]+[deoxyHb]) of total hemoglobin concentration change and optical path length (n=1, 2, ..., 24) based on the twenty-four second information of the amount of received light $\Delta A2_n(\lambda_1)$, $\Delta A2_n(\lambda_2)$, and $\Delta A2_n(\lambda_3)$ stored in the data storage region 23b by using the relational equations (1), (2) and (3).

Here, for the sake of description, the function processed by the analysis control element 40 is divided into blocks: a first mixing matrix generating element 43, a second mixing matrix generating element 44, a removal target first independent component signal determination element 45, a removal target second independent component signal determination element 46, and a restructuring element 47 for generating removal target component removal observation signals $X_n'(t)$.

The first mixing matrix generating element 43 controls, as shown by the formula (7), separation of the twelve first observation signals $U_m(t)$ into products of a 12×12 first mixing matrix and twelve first independent component signals $U_m(t)$ through independent component analysis.

The second mixing matrix generating element 44 controls, as shown by an expression (4), separation of the twenty-four second observation signals $X_n(t)$ into products of a 24×24 second mixing matrix and twenty-four second independent component signals $S_n(t)$ through independent component analysis.

The removal target first independent component signal determination element 45 controls finding of maximum threshold mixing coefficients $b_{max}$ from among each line vector in the 12×12 first mixing matrix, and finding of a removal target first independent component signal based on the number of maximum mixing coefficients $b_{max}$ present in each column vector (for example, 2 or more).

For example, twelve maximum mixing coefficients $b_{max}$ in total are found in the 12×12 first mixing matrix such that the maximum mixing coefficient $b_{max}$ is found from among mixing coefficients $b_{11}$ to $b_{1m}$ in a first line vector, and the maximum mixing coefficient $b_{max}$ is found from among mixing coefficients $b_{21}$ to $b_{2m}$ in a second line vector. Then, the number of the maximum mixing coefficients $b_{max}$, present in each column vector is calculated such that the number of the maximum mixing coefficients $b_{max}$ present in a first column vector is calculated and the number of the maximum mixing coefficients $b_{max}$ present in a second column vector is calculated. The first independent component signals $U_m(t)$ corresponding to column vectors where the number of the maximum mixing coefficients $b_{max}$ is, for example, two or more are determined as the removal target first independent component signal. For example, as shown by the formula (8), when the number of the maximum mixing coefficients $b_{max}$ present in the second column vector is two or more and the number of the maximum mixing coefficients $b_{max}$ present in the first column vector and a third column vector to a twelfth column vector are less than two, the signals are determined as a removal target first independent component signal $U_2(t)$.

The removal target second independent component signal determination element 46 controls calculation of correlation coefficients $\alpha_n$ between the removal target first independent component signal $U_2(t)$ and each of the second independent component signals $S_n(t)$ (n=1, 2, ..., 24), and determination of a signal where the correlation coefficient $\alpha_n$ is a threshold $\alpha_{th}$ or more as a removal target second independent component signal.

For example, twenty-four correlation coefficients $\alpha_n$ in total are calculated such that a correlation coefficient $\alpha_1$ between the removal target first independent component signal $U_2(t)$ and the second independent component signal $S_1(t)$ is calculated, and a correlation coefficient $\alpha_2$ between the removal target first independent component signal $U_2(t)$ and the second independent component signal $S_2(t)$ is calculated. The second independent component signals $S_n(t)$ where the correlation coefficients $\alpha_n$ are the threshold $\alpha_{th}$ or more in the twenty-four second independent component signals $S_n(t)$ are determined as the removal target second independent component signal. For example, when the correlation coefficient $\alpha_1$ is the threshold $\alpha_{th}$ or more and the correlation coefficients $\alpha_2$ to $\alpha_{24}$ are less than the threshold $\alpha_{th}$, the signals are determined as the removal target second independent component signal $S_1(t)$.

The restructuring element 47 controls generation of a removal target component removal mixing matrix where 0 is substituted for a column vector corresponding to the removal target second independent component signal $S_1(t)$, and multiplication of a 24×24 removal target component removal mixing matrix by twenty-four independent component signals $S_n(t)$, so as to generate the twenty-four removal target component removal observation signals $X_n'(t)$.

Figure 6:
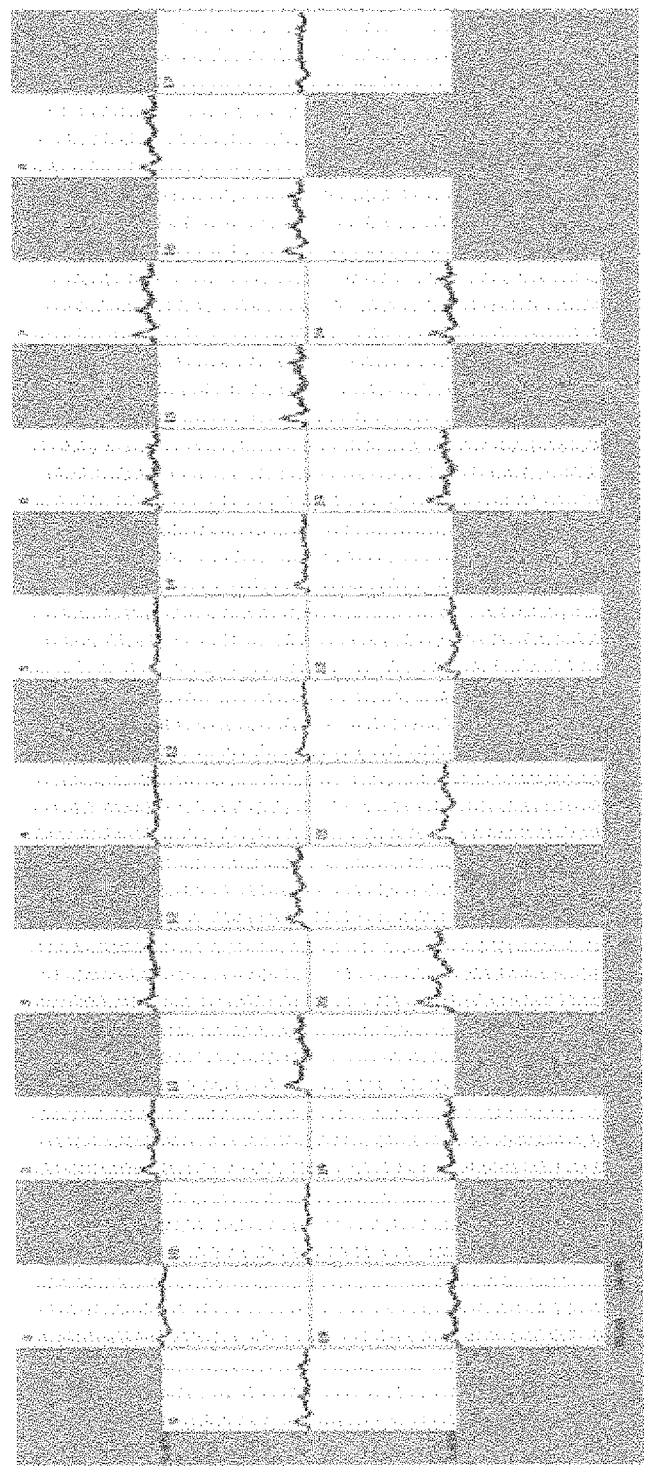
FIG. 6 is a diagram illustrating a monitor screen on which twenty-four removal target component removal observation signals $X_n'(t)$ are displayed.

For example, as shown by the formula (5), when such a signal is the removal target second independent component signal $S_1(t)$, a removal target component removal mixing matrix where 0 is substituted for the first column vector is generated. The 24×24 removal target component removal mixing matrix is multiplied with the twenty-four independent component signals $S_n(t)$ so that the twenty-four removal target component removal observation signals $X_n'(t)$ are generated. As a result, the twenty-four removal target component removal observation signals $X_n'(t)$ shown in FIG. 6 are obtained.

Figure 7:
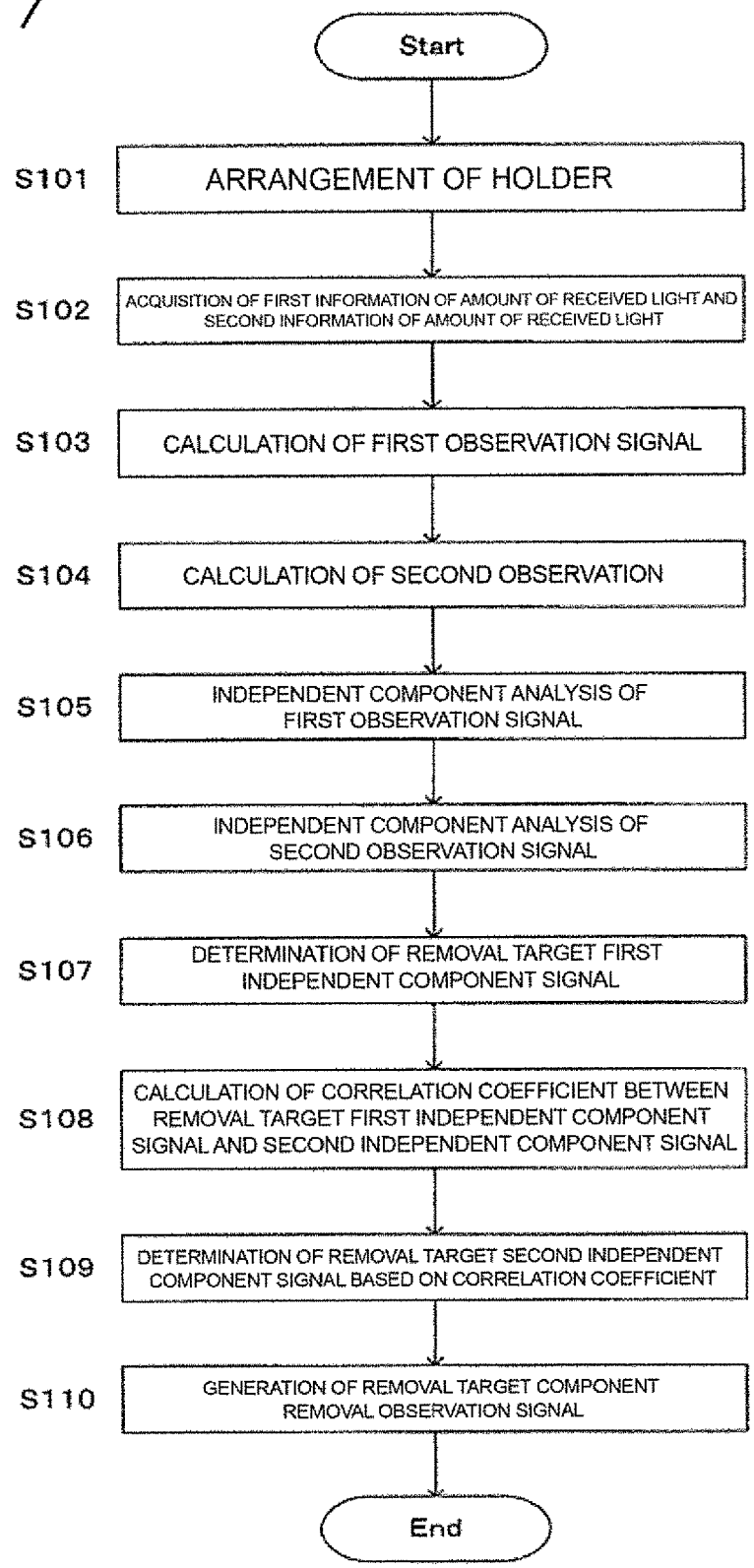
FIG. 7 is a flowchart for describing one example of an analysis method for the optical biological measuring device.
Figure 8:
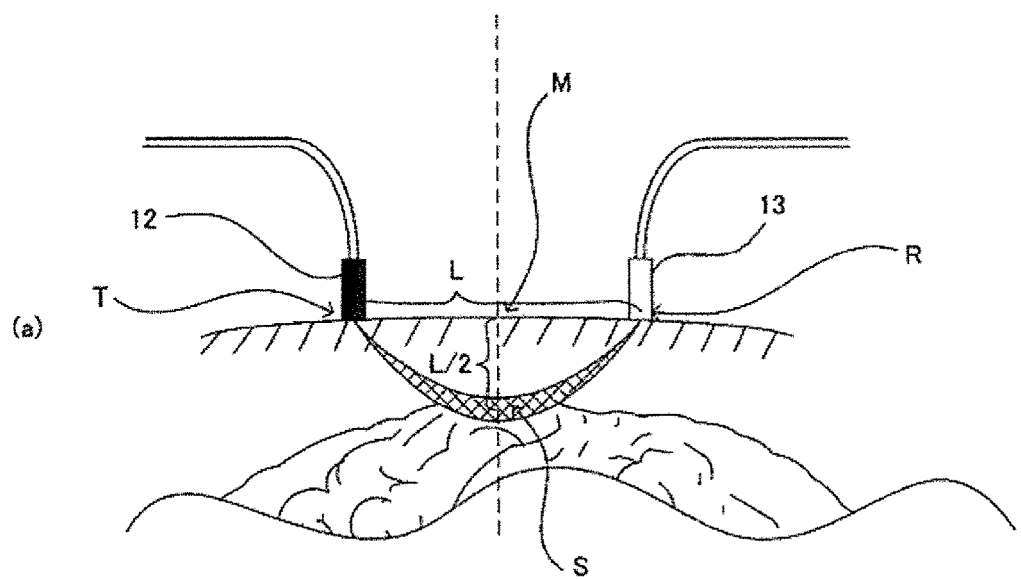
FIGS. 8A and 8B are diagrams illustrating a relationship between a pair of the light transmission probe and the light reception probe, and a measurement site.
Figure 8:
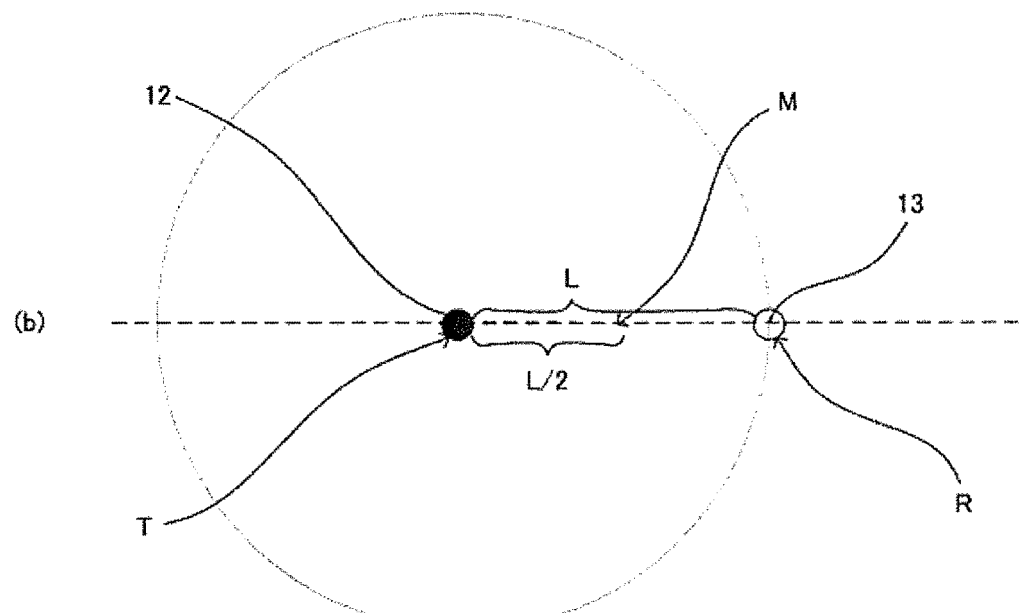
Figure 9:
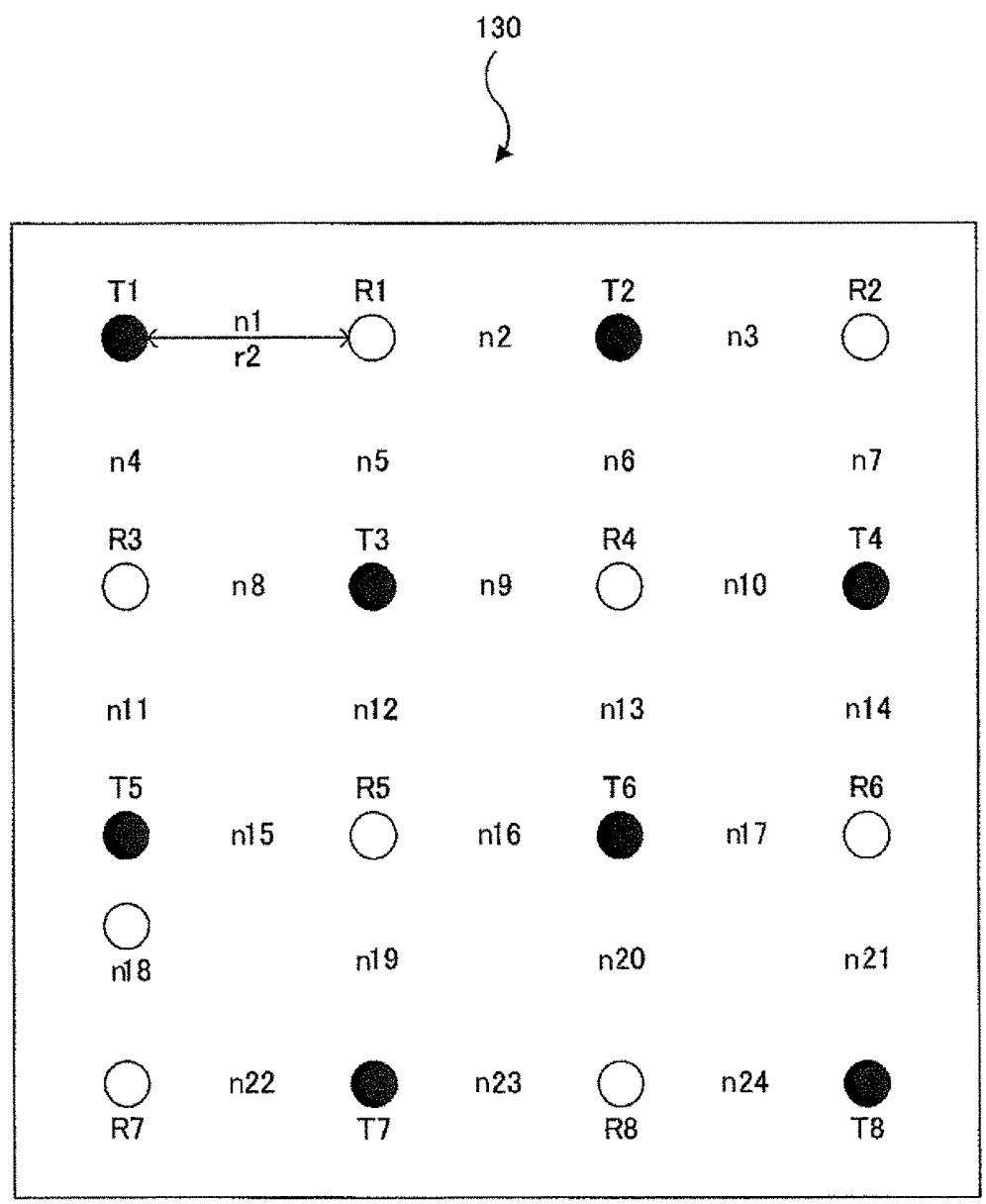
FIG. 9 is a plan diagram illustrating one example of a holder into which the eight light transmission probes and the eight light reception probes are inserted.
Figure 10:
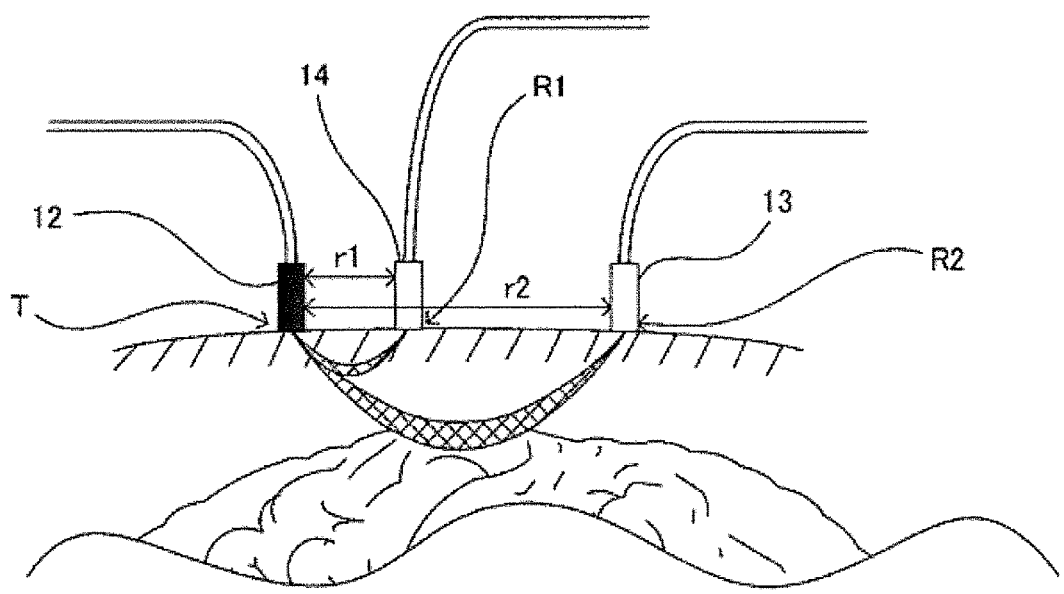
FIG. 10 is a cross-sectional diagram illustrating a relationship between the light transmission probe, the reference probe for a short distance r1 and the light reception probe for a long distance r2, and the measurement site.

An analysis method for the optical biological measuring device 1 is described below. FIG. 7 is a flowchart for describing one example of the analysis method for the optical biological measuring device 1.

First, the holder 30 is arranged on the scalp surface of a subject at step S101.

Next, in processing at step S102, the light transmission/reception control element 21 outputs a driving signal for transmitting light to one light transmission probe 12 at a predetermined time based on the control table stored in the control table storage region 23a to the light source driving mechanism 4, and detects, with the light detector 3, the information of the amount of received light $\Delta A1_m(\lambda_1)$, $\Delta A1_m(\lambda_2)$, $\Delta A1_m(\lambda_3)$, $\Delta A2_n(\lambda_1)$, $\Delta A2_n(\lambda_2)$ and $\Delta A2_n(\lambda_3)$ (m=1, 2, . . . , 12, and n=1, 2, . . . , 24) received by the light reception probes 13 and the reference probes 14.

Next, in processing at step S103, the first observation signal acquiring element 24 obtains the time-course variations (first observation signals) $H_m(t)$ (m=1, 2, . . . , 12) of the product [oxyHb] of oxyhemoglobin concentration change and optical path length based on the twelve first information of the amount of received light $\Delta A1_m(\lambda_1)$, $\Delta A1_m(\lambda_2)$ and $\Delta A1_m(\lambda_3)$ stored in the data storage region 23b by using the relational equations (1), (2) and (3).

Next, in processing at step S104, the second observation signal acquiring element 25 obtains the time-course variations (second observation signals) $X_n(t)$ (n=1, 2, . . . , 24) of the product [oxyHb] of oxyhemoglobin concentration change and optical path length based on the twenty-four second information of the amount of received light $\Delta A2_n(\lambda_1)$, $\Delta A2_n(\lambda_2)$ and $\Delta A2_n(\lambda_3)$ stored in the data storage region 23b by using the relational equations (1), (2) and (3).

Next, in processing at step S105, the first mixing matrix generating element 43, as shown by the formula (7), separates the twelve first observation signals $H_m(t)$ into products of the 12×12 first mixing matrix and the twelve first independent component signals $U_m(t)$ through independent component analysis.

Next, in processing at step S106, the second mixing matrix generating element 44, as shown by the formula (4), separates the twenty-four first observation signals $X_n(t)$ into products of the 24×24 first mixing matrix and the twenty-four second independent component signals $S_n(t)$ (second mixing matrix generating step) through independent component analysis.

Next, in processing at step S107, the removal target first independent component signal determination element 45 finds the maximum threshold mixing coefficients $b_{max}$ from among each line vector in the 12×12 first mixing matrix, and finds the removal target first independent component signal $U_2(t)$ based on the number of the maximum mixing coefficients $b_{max}$ preset in each column vector (for example, two or more).

Next, in processing at step S108, the removal target second independent component signal determination element 46 calculates the correlation coefficients $\alpha_n$ between the removal target first independent component signal $U_2(t)$ and each of the second independent component signals $S_n(t)$ (n=1, 2, . . . , 24).

Next, in processing at step S109, the removal target second independent component signal determination element 46 determines a signal where the correlation coefficient $\alpha_n$ is the threshold $\alpha_{th}$ or more as the removal target second independent component signal $S_1(t)$ (removal target second independent component signal determining step).

Next, in processing at step S110, the restructuring element 47, as shown by the formula (5), generates the removal target component removal mixing matrix where 0 is substituted for a column vector corresponding to the removal target second independent component signal $S_1(t)$, and multiplies the 24×24 removal target component removal mixing matrix by the twenty-four independent component signals $S_n(t)$, so as to generate the twenty-four removal target component removal observation signals $X_n'(t)$ (restructuring step).

When step S110 is finished, this flowchart will end.

It is noted, that the analysis control electronic device that generates a removal target component removal observation signal value based upon a correlation coefficient between the first observation signal value and the second observation signal value, the correlation coefficient being provided by the following equation: $\rho_{X,Y} = \text{cov}(X,Y) / \rho_X \rho_Y$, where X =first independent component signal, Y =second independent component signal, cov is the covariance, $\rho_X$ is the standard deviation of X, and $\rho_Y$ is the standard deviation of Y; and wherein the device removes the target component removal observation signal value thereby providing a diagnosis of a cerebral symptom based upon a regionally measured portion of a brain of the subject.

As described above, in the optical biological measuring device 1, the independent component analysis is made on the twelve first observation signals $H_m(t)$ so that the removal target first independent component signal $U_2(t)$ is found from among the twelve first independent component signals $U_m(t)$. Further, the removal target second independent component signal $S_1(t)$ is found from among the twenty-four second independent component signals $S_n(t)$ by using the removal target first independent component signal $U_2(t)$. For this reason, it is possible to accurately diagnose whether or not symptoms such as cerebral ischemia are generated also in the case of regionally measuring the brain.

Another Alternative Embodiment(s)

(1) The above optical biological measuring device 1 has the configuration such that the maximum threshold mixing coefficients $b_{max}$ are found from among each line vector in the 12×12 first mixing matrix, and the removal target first independent component signal is found based on the number of the maximum mixing coefficients $b_{max}$ present in each column vector (for example, two or more). However, it may have a configuration such that the threshold mixing coefficients $b_{over}$ that are a threshold $b_{th}$ or more are found from among each line vector in the 12×12 first mixing matrix, and the removal target first independent component signal is found based on the number of the threshold mixing coefficients $b_{over}$ in each column vector (for example, two or more.)

(2) The above optical biological measuring device 1 has the configuration such that the removal target component removal observation signals $X_n'(t)$ are generated for the time-course (chronological) variations (second observation signal) $X_n(t)$ of the product [oxyHb] of oxyhemoglobin concentration change and optical path length. However, it may have a configuration such that removal target component removal observation signals $Y_n'(t)$ are generated for time-course variations (second observation signal) $Y_n(t)$ of a product [deoxyHb] of deoxyhemoglobin concentration change and optical path length, or removal target component removal observation signals $Z_n'(t)$ are generated for time-course variations (second observation signal) $Z_n(t)$ of a product ([oxyHb]+[deoxyHb]) of total hemoglobin concentration change and optical path length.

(3) The above optical biological measuring device 1 has the configuration such that the holder 30 is used which has the eight light transmission probes $12_{T1}$ to $12_{T8}$, the eight light reception probes $13_{R1}$ to $13_{R8}$, and the twelve reference probes $14_{B1}$ to $14_{B12}$, but may have a configuration such that a first holder is used which has the eight light transmission probes $12_{T1}$ to $12_{T8}$ and the eight light reception probes $13_{R1}$ to $13_{R8}$, and a second holder is used which has the twelve reference probes $14_{B1}$ to $14_{B12}$.

(4) The above optical biological measuring device 1 has the configuration such that the independent component analysis is made on the twelve first observation signals $H_m(t)$, but may have a configuration such that one first observation signal $H_m(t)$ is used.

INDUSTRIAL APPLICABILITY

The present invention can be applied for an optical biological measurement device and so forth, which measures noninvasively brain activities.

It will be further understood by those of skill in the arts, after having studied the disclosure herein, that the modules, computer, and features herein shall be understood to contain all necessary components, features, processors, memory devices, and related elements shall be operative and effective to achieve the noted result without departing from the scope herein, whereby as a non-limiting example, a step of calculating shall be conducted in a suitable processor component for related signals and data contain and shall contain all the needed operative functions to achieve such goals and steps as discussed herein as will be recognized within the scope and skill of the art. As a non-limiting listing such as processor controls, memory devices, operative software, input/output features, and related elements shall be otherwise effective to render the proposed aspects, features, methods and or steps herein fully operative within the scope and spirit of the present invention and those of skill in the art.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE OF SIGN

1 Optical biological measurement device
12 Light transmission probe
13 Light reception probe
14 Reference probe
21 Light transmission/reception control element
23 Memory
24 First observation signal acquiring element
25 Second observation signal acquiring element
30 Holder (light transmission/reception element)
40 Analysis control element
44 Second mixing matrix generating element
46 Removal target second independent component signal determination element
47 Restructuring element

What is claimed is:

1. An optical biological measuring device for removing a signal corresponding to a removal target component when measuring a local area of a brain, comprising:
a plurality of light transmission probes configured to be arranged on a scalp surface of a subject;
a plurality of light reception probes configured to be arranged on positions that are also separated from said light transmission probes on said scalp surface by a second setting distance r2; and
reference probes configured to be arranged on positions separated from said light transmission probes or said light reception probes on said scalp surface by a first setting distance r1 shorter than the second setting distance r2;
a first observation signal value configured to acquire first information values of an amount of received light ΔA1 from said light transmission probes to said reference probes so as to acquire said first observation signal value indicating a biological signal in an optical path of the distance r1 between the light transmission probes and the reference probes;
a second observation signal value configured to acquire acquiring second information values of an amount of received light ΔA2 from said light transmission probes to said light reception probes so as to acquire said second observation signal values indicating a biological signal in an optical path of the distance r2 between the light transmission probes and the light reception probes; and
an analysis control electronic device configured to generate a removal target component removal observation signal value based on respective said first observation signal value and said second observation signal value, wherein:
said analysis control electronic device, further comprises:
a second mixing matrix generating electronic device configured to separate a plurality of said second observation signal values into products of a second mixing matrix and a plurality of second independent component signal values through independent component analysis,
a removal target second independent component signal determination electronic device configured to find a removal target second independent component signal value from among the plurality of second independent component signal values using said first observation signal value, and
a restructuring electronic device configured to remove the removal target second independent component signal value from said second observation signal value so as to generate a plurality of removal target component removal observation signals;
a first mixing matrix generating electronic device configured to separate a plurality of first observation signal values into products of a first mixing matrix and a plurality of first independent component signal values through independent component analysis, and
a removal target first independent component signal determination electronic device for finding a removal target first independent component signal value from among the plurality of first independent component signals values;

wherein said removal target second independent component signal determination electronic device configured to calculate a correlation coefficients between the removal target first independent component signal value and the second independent component signal value, and determines a signal where the correlation coefficient is a threshold or more as the removal target second independent component signal value, and said removal target component removal observation signal value is determined based on the correlation coefficient between the removal target first independent component signal and the second independent component signals, the correlation coefficient being provided by the following equation:

$\rho_{X,Y} = \text{cov}(X,Y)/\rho_X \rho_Y$, where $X$=first independent component signal, $Y$=second independent component signal, cov is the covariance, $\rho_X$ is the standard deviation of $X$, and $\rho_Y$ is the standard deviation of $Y$; and wherein said optical biological measuring device is configured to remove said target component removal observation signal value thereby providing a diagnosis of a cerebral symptom based upon a regionally measured portion of the brain.

2. The optical biological measuring device according to claim 1, wherein:
said removal target first independent component signal determination electronic device configured to find a maximum mixing coefficient from among each line vector in said first mixing matrix, and finds said removal target first independent component signal based on a number of the maximum mixing coefficients present in each column vector.

3. The optical biological measuring device according to claim 1, wherein:
said removal target first independent component signal determination electronic device configured to find a threshold mixing coefficient that is a threshold or more from among each line vector in said first mixing matrix, and finds said removal target first independent component signal based on a number of the threshold mixing coefficients present in each column vector.

4. The optical biological measuring device according to claim 1, wherein:
said restructuring electronic device substitutes 0 for a column vector corresponding to the removal target second independent component signal value in said second mixing matrix so as to generate a removal target component removal mixing matrix, and multiplies the removal target component removal mixing matrix by the plurality of second independent component signal values, so as to generate the plurality of removal target component removal observation signal values.

5. An analysis method, for generating a removal target component removal observation signal value based on a first observation signal value and a second observation signal value using an optical biological measuring device comprising the steps of:
providing a light transmission/reception electronic device having:
a plurality of light transmission probes arranged on a scalp surface of a subject;
a plurality of light reception probes arranged on positions that are also on said scalp surface and separated from said light transmission probes on said scalp surface by a second setting distance r2; and
reference probes arranged on positions separated from said light transmission probes or said light reception probes on said scalp surface by a first setting distance r1 shorter than the second setting distance r2;

providing a first observation signal value acquiring electronic device for acquiring first information values of an amount of received light $\Delta A1$ from said light transmission probes or said light reception probes to said reference probes so as to acquire the first observation signal value indicating a biological signal in an optical path of the distance r1 between the light transmission probes and the light reception probes; and providing a second observation signal value acquiring electronic device for acquiring second information values of an amount of received light $\Delta A2$ from said light transmission probes to said light reception probes so as to acquire the second observation signal value indicating a biological signal in an optical path of the distance r2 between the light transmission probes and the light reception probes, and providing an analysis control electronic device that generates a removal target component removal observation signal value based on said first observation signal value and said second observation signal value, wherein the analysis method further comprises the steps of:
conducting a second mixing matrix generating step of separating a plurality of second observation signal values into products of a second mixing matrix and a plurality of second independent component signal values through independent component analysis;
conducting a removal target second independent component signal value determining step of finding a removal target second independent component signal value from among the plurality of second independent component signal values using said first observation signal value; and
conducting a restructuring step of removing the removal target second independent component signal value from said second observation signal value so as to generate a plurality of removal target component removal observation signal values;
providing a plurality of reference probes arranged in said light transmission/reception electronic device,
said analysis control electronic device, further comprising:
a first mixing matrix generating electronic device for separating a plurality of first observation signal values into products of a first mixing matrix and a plurality of first independent component signal value through independent component analysis, and
a removal target first independent component signal determination electronic device for finding a removal target first independent component signal value from among the plurality of first independent component signal values,
operating said removal target second independent component signal value determination electronic device to calculate correlation coefficients between the removal target first independent component signal value and the second independent component signal values, and determining a signal value where the correlation coefficient is a threshold or more as the removal target second independent component signal value, and said removal target component removal observation signal value is determined based on the correlation coefficient between the removal target first independent component signal and the removal target second independent component signal, the correlation coefficient being provided by the following equation:

$\rho_{X,Y}=\text{cov}(X,Y)/\rho_X\rho_Y$, where $X$=the removal target first independent component signal, $Y$=the removal target second independent component signal, cov is the covariance, $\rho_X$ is the standard deviation of $X$, and $\rho_Y$ is the standard deviation of $Y$; and wherein said analysis method removes said target component removal observation signal value thereby providing a diagnosis of a cerebral symptom based upon a regionally measured portion of a brain.

6. The analysis method, according to claim 5, further comprising the steps of:
operating said removal target first independent component signal value determination electronic device to find a maximum mixing coefficient from among each line vector in said first mixing matrix, and finding said removal target first independent component signal value based on a number of the maximum mixing coefficients present in each column vector.

7. The analysis method, according to claim 6, further comprising the steps of:
operating said removal target first independent component signal value determination electronic device to find a threshold mixing coefficient that is a threshold or more from among each line vector in said first mixing matrix, and finding said removal target first independent component signal value based on a number of the threshold mixing coefficients present in each column vector.

8. The analysis method, according to claim 5, wherein:
said restructuring electronic device substitutes 0 for a column vector corresponding to the removal target second independent component signal value in said second mixing matrix and generating a removal target component removal mixing matrix, and multiplying the removal target component removal mixing matrix by the plurality of second independent component signal values, and generating a plurality of removal target component removal observation signal value.

9. An optical biological measuring device for removing a signal corresponding to a removal target component when measuring a local area of a brain, comprising:
a first mixing matrix generating electronic device configured to separate a plurality of first observation signal values into products of a first mixing matrix and a plurality of first independent component signal value through independent component analysis;
an analysis control electronic device configured to generate a removal target component removal observation signal value based on said first observation signal value and said second observation signal value; wherein an analysis method conducted by the analysis control electronic device further comprises the steps of:
conducting a second mixing matrix generating step of separating a plurality of second observation signal values into products of a second mixing matrix and a plurality of second independent component signal values through independent component analysis;
conducting a removal target second independent component signal value electronic value determining step of finding a removal target second independent component signal value from among the plurality of second independent component signal values using said first observation signal value; and
conducting a restructuring step of removing the removal target second independent component signal value from said second observation signal value so as to generate a plurality of removal target component removal observation signal values;
providing a plurality of reference probes arranged in said light transmission/reception electronic device;
a plurality of light transmission probes arranged on a scalp surface of a subject;
a plurality of light reception probes arranged on a scalp surface on positions separated from said light transmission probes on said scalp surface by a second setting distance r2; and
a plurality of reference probes arranged on positions separated from said light transmission probes on said scalp surface by a first setting distance r1 shorter than the second setting distance r2;
a first observation signal value acquiring electronic device configured to acquire a first information value of an amount of received light $\Delta A1$ from said light transmission probes or said light reception probes to said reference probes so as to acquire a first observation signal value indicating biological signal in an optical path of the distance r1 between the light transmission probes and the light reception probes;
a second observation signal value acquiring electronic device configured to acquire a second information value of an amount of received light $\Delta A2$ from said light transmission probes to said light reception probes so as to acquire a second observation signal value indicating a biological signal in an optical path of the distance r2 between the light transmission probes and said light reception probes;
the analysis control electronic device configured to generate a removal target component removal observation signal value based upon a correlation coefficient between said first observation signal value and said second observation signal value, the correlation coefficient being provided by the following equation:

$\rho_{X,Y}=\text{cov}(X,Y)/\rho_X\rho_Y$, where $X$=first independent component signal, $Y$=second independent component signal, cov is the covariance, $\rho_X$ is the standard deviation of $X$, and $\rho_Y$ is the standard deviation of $Y$; and wherein said optical biological measuring device is configured to remove said target component removal observation signal value thereby providing a diagnosis of a cerebral symptom based upon a regionally measured portion of the brain of said subject.

* * * * *